(12) United States Patent
Goraltchouk et al.

(10) Patent No.: US 8,641,732 B1
(45) Date of Patent: Feb. 4, 2014

(54) SELF-RETAINING SUTURE WITH VARIABLE DIMENSION FILAMENT AND METHOD

(75) Inventors: Alexei Goraltchouk, Richmond (CA); Alexander Naimagon, Richmond (CA); Gerald F. Cummings, Port Moody (CA); Lev Drubetsky, Coquitlam (CA); Robert A. Herrmann, Vancouver (CA)

(73) Assignee: Ethicon, Inc., Somerville, NJ (US)

( * ) Notice: Subject to any disclaimer, the term of this patent is extended or adjusted under 35 U.S.C. 154(b) by 533 days.

(21) Appl. No.: 12/392,955

(22) Filed: Feb. 25, 2009

Related U.S. Application Data

(60) Provisional application No. 61/031,579, filed on Feb. 26, 2008.

(51) Int. Cl.
 *A61B 17/04* (2006.01)

(52) U.S. Cl.
 USPC ............................................. 606/228

(58) Field of Classification Search
 USPC .................. 606/228–232, 219; 264/167
 See application file for complete search history.

(56) References Cited

U.S. PATENT DOCUMENTS

| | | |
|---|---|---|
| 709,392 A | 9/1902 | Brown |
| 733,723 A | 7/1903 | Lukens |
| 789,401 A | 5/1905 | Acheson |
| 816,026 A | 3/1906 | Meier |
| 897,958 A | 2/1908 | Foster |
| 1,142,510 A | 6/1915 | Engle |
| 1,248,825 A | 12/1917 | Dederrer |
| 1,321,011 A | 11/1919 | Cottes |
| 1,558,037 A | 10/1925 | Morton |
| 1,728,316 A | 9/1929 | Wachenfeldt |
| 1,886,721 A | 11/1932 | O'Brien |
| 2,094,578 A | 10/1937 | Blumenthal et al. |
| 2,201,610 A | 5/1940 | Dawson |
| 2,232,142 A | 2/1941 | Schumann |
| 2,254,620 A | 9/1941 | Miller |
| 2,347,956 A | 5/1944 | Lansing |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

Bellin et al., "Polymeric triple-shape materials", Proceedings of the National Academy of Sciences of the United States of America Nov. 28, 2006; 2103(48):18043-18047.

(Continued)

*Primary Examiner* — Julian W Woo

(57) ABSTRACT

A self-retaining suture comprises a variable-dimension filament which varies in size and/or shape along the length of the filament. The variation in size and/or shape results in a variation in the distribution of filament material from one region of the filament to the next. The filament has retainers formed in the surface such that the filament can engage and retain tissue. The retainers are formed in a manner that makes use of regions of the filament where additional material is distributed. The resulting self-retaining suture has a greater minimum cross-section than would be created using an equivalent uniform filament. The resulting self-retaining suture consequently has a greater tensile strength. Methods for manufacturing the filament and retainers are also described.

13 Claims, 6 Drawing Sheets

(56) References Cited

U.S. PATENT DOCUMENTS

| | | |
|---|---|---|
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Eaton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski |
| 3,066,452 A | 12/1962 | Bott et al. |
| 3,066,673 A | 12/1962 | Bott et al. |
| 3,068,869 A | 12/1962 | Shelden |
| 3,068,870 A | 12/1962 | Levin |
| 3,123,077 A | 3/1964 | Alcamo |
| 3,166,072 A | 1/1965 | Sullivan |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling et al. |
| 3,385,299 A | 5/1968 | Le Roy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A * | 3/1973 | de Mestral et al. ........... 264/167 |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal et al. |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn et al. |
| 4,311,002 A | 1/1982 | Dipalma et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey et al. |
| 4,434,796 A | 3/1984 | Karapetian et al. |
| 4,449,298 A | 5/1984 | Putz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,719,917 A | 1/1988 | Barrows et al. |
| 4,741,330 A | 5/1988 | Hayhurst |
| 4,750,910 A | 6/1988 | Takayanagi et al. |
| 4,751,621 A | 6/1988 | Jenkins |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schutz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini |
| 4,981,149 A | 1/1991 | Yoon et al. |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |

(56) References Cited

U.S. PATENT DOCUMENTS

| | | |
|---|---|---|
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson et al. |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green et al. |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | Dipalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch et al. |
| 5,522,845 A | 6/1996 | Wenstrom, Jr. et al. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,884,859 A | 3/1999 | Ma |
| 5,887,594 A | 3/1999 | Locicero, III |

(56) References Cited

U.S. PATENT DOCUMENTS

| | | |
|---|---|---|
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,645,228 B2 | 11/2003 | Renz |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Lendlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. et al. |
| 7,021,316 B2 | 4/2006 | Leiboff |
| 7,033,379 B2 | 4/2006 | Peterson |
| 7,037,984 B2 | 5/2006 | Lendlein et al. |
| 7,048,748 B1 | 5/2006 | Ustuner |
| 7,056,331 B2 | 6/2006 | Kaplan et al. |
| 7,056,333 B2 | 6/2006 | Walshe |

(56) References Cited

U.S. PATENT DOCUMENTS

| | | |
|---|---|---|
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmielding et al. |
| 7,211,088 B2 | 5/2007 | Grafton et |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,513,904 B2 | 4/2009 | Sulamanidze et al. |
| 7,514,095 B2 | 4/2009 | Nelson et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,919,112 B2 | 4/2011 | Pathak et al. |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,308,761 B2 | 11/2012 | Brailovski et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0044637 A1 | 11/2001 | Jacobs et al. |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0069617 A1 | 6/2002 | Dey et al. |
| 2002/0077448 A1 | 6/2002 | Antal et al. |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173807 A1 | 11/2002 | Jacobs |
| 2002/0173822 A1 | 11/2002 | Justin et al. |
| 2002/0179718 A1 | 12/2002 | Murokh et al. |
| 2003/0014077 A1 | 1/2003 | Leung et al. |
| 2003/0040795 A1 | 2/2003 | Elson et al. |
| 2003/0041426 A1 | 3/2003 | Genova et al. |
| 2003/0065360 A1 | 4/2003 | Jacobs et al. |
| 2003/0065402 A1 | 4/2003 | Anderson et al. |
| 2003/0069602 A1 | 4/2003 | Jacobs et al. |
| 2003/0074021 A1 | 4/2003 | Morriss et al. |
| 2003/0074023 A1 | 4/2003 | Kaplan et al. |
| 2003/0078604 A1 | 4/2003 | Walshe |
| 2003/0088270 A1 | 5/2003 | Lubbers et al. |
| 2003/0097150 A1 | 5/2003 | Fallin et al. |
| 2003/0105489 A1 | 6/2003 | Eichhorn et al. |
| 2003/0149447 A1* | 8/2003 | Morency et al. ............... 606/228 |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236550 A1 | 12/2003 | Peterson et al. |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0028655 A1 | 2/2004 | Nelson et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0059378 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0093028 A1 | 5/2004 | Ruff |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0226427 A1 | 11/2004 | Trull et al. |
| 2004/0230223 A1 | 11/2004 | Bonutti et al. |
| 2004/0237736 A1 | 12/2004 | Genova et al. |
| 2004/0254609 A1 | 12/2004 | Esplin |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0033367 A1 | 2/2005 | Leung et al. |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki et al. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0106211 A1 | 5/2005 | Nelson et al. |
| 2005/0113936 A1 | 5/2005 | Brustad et al. |
| 2005/0119694 A1 | 6/2005 | Jacobs et al. |

(56) References Cited

U.S. PATENT DOCUMENTS

| | | |
|---|---|---|
| 2005/0125020 A1 | 6/2005 | Meade et al. |
| 2005/0125034 A1 | 6/2005 | Cichocki, Jr. |
| 2005/0125035 A1 | 6/2005 | Cichocki et al. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen et al. |
| 2006/0020272 A1 | 1/2006 | Gildenberg |
| 2006/0030884 A1 | 2/2006 | Yeung et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff et al. |
| 2006/0135995 A1 | 6/2006 | Ruff et al. |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Lendlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0156175 A1 | 7/2007 | Weadock et al. |
| 2007/0167958 A1 | 7/2007 | Sulamanidze et al. |
| 2007/0187861 A1 | 8/2007 | Genova et al. |
| 2007/0208355 A1 | 9/2007 | Ruff |
| 2007/0208377 A1 | 9/2007 | Kaplan et al. |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |

(56) References Cited

U.S. PATENT DOCUMENTS

| | | | |
|---|---|---|---|
| 2009/0299407 | A1 | 12/2009 | Yuan et al. |
| 2009/0299408 | A1 | 12/2009 | Schuldt-Hempe et al. |
| 2009/0306710 | A1 | 12/2009 | Lindh et al. |
| 2010/0021516 | A1 | 1/2010 | McKay |
| 2010/0023055 | A1 | 1/2010 | Rousseau |
| 2010/0057123 | A1 | 3/2010 | D'Agostino et al. |
| 2010/0063540 | A1 | 3/2010 | Maiorino |
| 2010/0071833 | A1 | 3/2010 | Maiorino |
| 2010/0087855 | A1 | 4/2010 | Leung et al. |
| 2010/0101707 | A1 | 4/2010 | Maiorino et al. |
| 2010/0140115 | A1 | 6/2010 | Kirsch |
| 2010/0160961 | A1 | 6/2010 | Nawrocki et al. |
| 2010/0163056 | A1 | 7/2010 | Tschopp et al. |
| 2010/0211097 | A1 | 8/2010 | Hadba et al. |
| 2010/0211098 | A1 | 8/2010 | Hadba et al. |
| 2010/0239635 | A1 | 9/2010 | McClain et al. |
| 2010/0292718 | A1 | 11/2010 | Sholev et al. |
| 2010/0294103 | A1 | 11/2010 | Genova et al. |
| 2010/0294104 | A1 | 11/2010 | Genova et al. |
| 2010/0294105 | A1 | 11/2010 | Genova et al. |
| 2010/0294106 | A1 | 11/2010 | Genova et al. |
| 2010/0294107 | A1 | 11/2010 | Genova et al. |
| 2010/0298637 | A1 | 11/2010 | Ruff |
| 2010/0298867 | A1 | 11/2010 | Ruff |
| 2010/0298868 | A1 | 11/2010 | Ruff |
| 2010/0298871 | A1 | 11/2010 | Ruff et al. |
| 2010/0298878 | A1 | 11/2010 | Leung et al. |
| 2010/0298879 | A1 | 11/2010 | Leung et al. |
| 2010/0298880 | A1 | 11/2010 | Leung et al. |
| 2010/0313723 | A1 | 12/2010 | Genova et al. |
| 2010/0313729 | A1 | 12/2010 | Genova et al. |
| 2010/0313730 | A1 | 12/2010 | Genova et al. |
| 2010/0318122 | A1 | 12/2010 | Leung et al. |
| 2010/0318123 | A1 | 12/2010 | Leung et al. |
| 2011/0009902 | A1 | 1/2011 | Leung et al. |
| 2011/0046669 | A1 | 2/2011 | Goraltchouk et al. |
| 2011/0106152 | A1 | 5/2011 | Kozlowski |
| 2011/0130774 | A1 | 6/2011 | Criscuolo et al. |
| 2011/0166597 | A1 | 7/2011 | Herrmann et al. |
| 2012/0109188 | A1 | 5/2012 | Viola |

FOREIGN PATENT DOCUMENTS

| | | |
|---|---|---|
| CN | 2640420 | 9/2004 |
| DE | P 1 810 800 | 6/1970 |
| DE | 03227984 | 2/1984 |
| DE | 43 02 895 | 8/1994 |
| DE | 19618891 | 4/1997 |
| DE | 19833703 | 2/2000 |
| DE | 10245025 | 4/2004 |
| DE | 10 2005 004317 | 6/2006 |
| EP | 0121362 | 9/1987 |
| EP | 0329787 | 8/1989 |
| EP | 0428253 | 5/1991 |
| EP | 0464479 | 1/1992 |
| EP | 0513713 | 5/1992 |
| EP | 0513736 | 11/1992 |
| EP | 0558993 | 9/1993 |
| EP | 0574707 | 12/1993 |
| EP | 0576337 | 12/1993 |
| EP | 0612504 | 8/1994 |
| EP | 0632999 | 1/1995 |
| EP | 0464480 | 3/1995 |
| EP | 0664198 | 7/1995 |
| EP | 0673624 | 9/1995 |
| EP | 0705567 | 4/1996 |
| EP | 0755656 | 1/1997 |
| EP | 0576337 B1 | 3/1997 |
| EP | 826337 | 3/1998 |
| EP | 0913123 | 5/1999 |
| EP | 0916310 | 5/1999 |
| EP | 0960600 | 12/1999 |
| EP | 1075843 | 2/2001 |
| EP | 0839499 | 9/2003 |
| EP | 1525851 | 4/2005 |
| EP | 1532942 | 5/2005 |
| EP | 1 726 317 | 11/2006 |
| EP | 0991359 | 11/2007 |
| EP | 2036502 | 3/2009 |
| EP | 1948261 | 11/2010 |
| EP | 2338421 | 11/2012 |
| FR | 2619129 | 2/1989 |
| FR | 2693108 | 1/1994 |
| FR | 9208059 | 3/1997 |
| GB | 267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 054116419 | 9/1979 |
| JP | 63288146 | 11/1988 |
| JP | 001113091 | 5/1989 |
| JP | 003-165751 | 7/1991 |
| JP | 4-096758 | 3/1992 |
| JP | 004-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-59235 | 2/2002 |
| JP | 2003-275217 | 9/2003 |
| JP | 2005-500119 | 1/2005 |
| JP | 2006-516902 | 7/2006 |
| JP | 2006-517112 | 7/2006 |
| JP | 2009-118967 | 6/2009 |
| KR | 10-2005-0072908 A | 7/2005 |
| KR | 6013299 | 2/2006 |
| KR | 2006-59142 | 6/2006 |
| NZ | 501224 | 3/2002 |
| NZ | 531262 | 12/2005 |
| RU | 1823791 | 6/1993 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | 96/06565 | 3/1966 |
| WO | 86/00020 | 1/1986 |
| WO | 87/01270 | 3/1987 |
| WO | WO 88/09157 | 12/1988 |
| WO | WO 89/05618 | 6/1989 |
| WO | WO 90/09149 | 8/1990 |
| WO | 90/14795 | 12/1990 |
| WO | 92/22336 | 12/1992 |
| WO | 95/16399 | 6/1995 |
| WO | 95/29637 | 11/1995 |
| WO | WO 9852473 | 11/1998 |
| WO | WO 98/55031 | 12/1998 |
| WO | WO 9921488 | 5/1999 |
| WO | WO 99/33401 | 7/1999 |
| WO | 99/52478 | 10/1999 |
| WO | 99/59477 | 11/1999 |
| WO | WO 99/62431 | 12/1999 |
| WO | 00/51685 | 9/2000 |
| WO | WO 00/51658 | 9/2000 |
| WO | WO 01/06952 | 2/2001 |
| WO | 01/56626 | 8/2001 |
| WO | 03/003925 | 1/2003 |
| WO | WO 03/001979 | 1/2003 |
| WO | WO 03/017850 | 3/2003 |
| WO | WO 03/045255 | 6/2003 |
| WO | WO 03/077772 | 9/2003 |
| WO | WO 03/092758 | 11/2003 |
| WO | 03/103733 | 12/2003 |
| WO | WO 03/103972 | 12/2003 |
| WO | WO 03/105703 | 12/2003 |
| WO | 2004/014236 | 2/2004 |
| WO | 2004/030517 | 4/2004 |
| WO | WO 2004/030520 | 4/2004 |
| WO | WO 2004/030704 | 4/2004 |
| WO | WO 2004/030705 | 4/2004 |

(56) References Cited

FOREIGN PATENT DOCUMENTS

| WO | WO 2004/062459 | 7/2004 |
|---|---|---|
| WO | 2004/100801 | 11/2004 |
| WO | WO 2004/112853 | 12/2004 |
| WO | 2005/016176 | 2/2005 |
| WO | 2005/074913 | 8/2005 |
| WO | WO 2005/096955 | 10/2005 |
| WO | WO 2005/096956 | 10/2005 |
| WO | 2005/112787 | 12/2005 |
| WO | WO 2006/005144 | 1/2006 |
| WO | WO 2006/012128 | 2/2006 |
| WO | WO 2006/061868 | 6/2006 |
| WO | 2006/082060 | 8/2006 |
| WO | WO 2006/079469 | 8/2006 |
| WO | WO 2006/099703 | 9/2006 |
| WO | 2006/138300 | 12/2006 |
| WO | WO 2007/005291 | 1/2007 |
| WO | WO 2007005296 | 1/2007 |
| WO | 2007/038837 | 4/2007 |
| WO | WO 2007/053812 | 5/2007 |
| WO | 2007/089864 | 8/2007 |
| WO | WO 2007/112024 | 10/2007 |
| WO | WO 2007/133103 | 11/2007 |
| WO | 2007/145614 | 12/2007 |
| WO | 2008/128113 | 10/2008 |
| WO | 2008/150773 | 12/2008 |
| WO | 2009/042841 | 4/2009 |
| WO | 2009/068252 | 6/2009 |
| WO | 2009/087105 | 7/2009 |
| WO | 2009/097556 | 8/2009 |
| WO | 2009/151876 | 12/2009 |
| WO | 2010/052007 | 5/2010 |
| WO | 2011/053375 | 5/2011 |

OTHER PUBLICATIONS

Bunnell, S., "Gig pull-out suture for tendons." J Bone Joint Surg Am. Jul. 1954;36-A(4):850-1.
Dattillo, Jr., Philip Paul, "Knotless Bi-directional Barbed Absorbable Surgical Suture", Dissertation submitted to the Graduate Faculty of North Carolina State University Textile Management and Technology Nov. 2002, 75 pages.
Delorenzi, C.L., "Barbed Sutures: Rationale and Technique." Aesthetic Surg J. Mar. 2006 26(2): 223-229.
Han, Hongtao et al., "Mating and Piercing Micromechanical Structures for Surface Bonding Applications", Proceedings of the 1991 Micro Electro Mechanical Systems (MEMS '91), An Investigation of Micro Structures, Sensors, Actuators, Machines and Robots, Feb. 1991, pp. 253-258.
Ingle, Nilesh P et al., "Barbed Suture Anchoring Strength: Applicability to Dissimilar Polymeric Materials", College of Textiles, North Carolina State University, 7th World Biomaterials Congress 2004, 1 page.
Ingle, Nilesh P et al., "Testing the Tissue-holding Capacity of Barbed Sutures", College of Textiles, North Carolina State University, Fiber Science—The Next Generation Oct. 17-19, 2005, New Jersey Institute of Technology, Newark, NJ, 4 pages.
International Search Report for PCT/US2007/074658 dated Jun. 12, 2007, 4 pages.
International Search Report for PCT/US2008/060127 dated Sep. 23, 2008, 8 pages.
International Search Report for PCT/US2008/0064921 dated Nov. 19, 2008, 8 pages.
International Search Report for PCT/US2008/075849 dated Mar. 18, 2009, 7 pages.
Jennings et al., "A new technique in primary tendon repair." Surg Gynecol Obstet Nov. 1952;95(5):597-600.
Kaminer, M. et al., "ContourLift™:A New Method of Minimally Invasive Facial Rejuvenation", Cosmetic Dermatology Jan. 2007; 20(1): 29-35.
Kelch et al., "Shape-memory Polymer Networks from Olio[(∈-hydroxycaproate)-co-glycolate]dimethacrylates and Butyl Acrylate with Adjustable Hydrolytic Degradation Rate", Biomacromolecules 2007;8(3):1018-1027.

Leung, J. et al., "Performance Enhancement of a Knotless Suture via Barb Geometry Modifications", 7th World Biomaterials Congress 2004, 1 page.
Leung, J. et al., "Barbed, Bi-directional Medical Sutures: Biomechanical Properties and Wound Closure Efficacy Study", 2002 Society for Biomaterials 28th Annual Meeting Transactions, 1 page.
Maitland et al., "Prototype laser-activated shape memory polymer foam device for embolic treatment of aneurysms", Journal of Biomedical Optics May/Jun. 2007;12(3): pp. 030504-1 to 030504-3.
Malina, M. et al., "Endovascular AAA Exclusion: Will Stents With Hooks and Barbs Prevent Stent-Graft Migration?", Journal of Endovascular Surgery 1998; 5; 310-317.
Mansberger, et al., "A New Type Pull-Out Wire for Tendon Surgery: A Preliminary Report", Department of Surgery, University Hospital and University of Maryland School of Medicine, Baltimore, Maryland, Received for Publication May 10, 1951, pp. 119-121.
Mason, M.L., "Primary and secondary tendon suture. A discussion of the significance of technique in tendon surgery." Surg Gynecol Obstet 70 (1940).
McKee, G.K., "Metal anastomosis tubes in tendon suture." The Lancet, May 26, 1945, 659-660.
McKenzie, A.R. "An Experimental Multiple Barbed Suture for the Long Flexor Tendons of the Palm and Fingers." J Bone Joint Surg. 49B-(3): 440, 1967.
Moran et al., "Bidirectional-Barbed Sutured Knotless Running Anastomosis v Classic van Velthovan in a Model System", Journal of Endourology Oct. 2007; 21(10); 1175-1177.
Murtha et al., "Evaluation of a Novel Technique for Wound Closure Using a Barbed Suture", Journal of the American Society of Plastic Surgeons 2006; 117(6); 1769-1780.
Paul, Malcolm, "Using Barbed Sutures in Open/Subperiosteal Midface Lifting", Aesthetic Surgery Journal Nov./Dec. 2006; 26(6):725-732.
Potenza, Austin, "Tendon Healing Within the Flexor Digital Sheath in the Dog: An Experimental Study", Journal of Bone & Joint Surgery Jan. 1962; 44A(1):49-64.
Pulvertaft, "Suture Materials and Tendon Junctures", American Journal of Surgery Mar. 1965; 109:346-352.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2 pages, 2004.
Singapore Search Report for Singapore Patent Application No. 200702625-5 dated Nov. 26, 2008, 8 pages.
Singapore Search Report for Singapore Patent Application No. 200702350-0 dated Nov. 26, 2008, 7 pages.
Singapore Search Report for Singapore Patent Application No. 200703688-2 dated Nov. 26, 2008, 8 pages.
Sulamanidze, MD, M.A., et al., "Removal of Facial Soft Tissue Ptosis with Special Threads." Dermatol Surg 2002; 28; pp. 367-371.
Szarmach, Robin et al., "An Expanded Surgical Suture and Needle Evaulation and Selection Program by a Healthcare Resource Management Group Purchasing Organization", Journal of Long-Term Effects of Medical Implants 2003; 13(3); 155-170.
Verdan, Claude, "Primary Repair of Flexor Tendons", Journal of Bone and Joint Surgery Jun. 1960; 42(4):647-657.
Communication from EPO re: 10000486 dated Apr. 4, 2011.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.

(56) References Cited

OTHER PUBLICATIONS

European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2008/060127 dated Oct. 13, 2009.
International Preliminary Report re: PCT/US2009/040545 dated Oct. 19, 2010.
International Search Report for PCT/US1998/10478 dated Sep. 23, 1998.
International Search Report for PCT/US2002/027525 dated Dec. 9, 2002, 3 pages.
International Search Report for PCT/2003/30666 dated Dec. 15, 2004.
International Search Report for PCT/US2003/25088 dated Dec. 29, 2003.
International Search Report re: PCT/US2003/030674 dated Sep. 2, 2004.
International Search Report for PCT/US2009/040545 dated Oct. 29, 2009.
Partial European Search Report re: EP05025816 dated Mar. 20, 2006.
Supplementary European Search Report re: EP98923664 dated Jun. 12, 2001.
Supplementary European Search Report re: EP03752630 dated Nov. 17, 2005.
Supplementary European Search Report re: EP03785177 dated May 19, 2009.
U.S. Appl. No. 08/859,887, filed May 21, 1997.
U.S. Appl. No. 09/896,455, filed Jun. 29, 2001.
U.S. Appl. No. 09/919,750, filed Jul. 31, 2001.
U.S. Appl. No. 09/943,733, filed Aug. 31, 2001.
U.S. Appl. No. 10/216,516, filed Aug. 9, 2002.
U.S. Appl. No. 10/065,280, filed Sep. 30, 2002.
U.S. Appl. No. 10/065,279, filed Sep. 30, 2002.
U.S. Appl. No. 10/065,278, filed Sep. 30, 2002.
U.S. Appl. No. 10/914,755, filed Aug. 9, 2004.
U.S. Appl. No. 10/941,347, filed Sep. 15, 2004.
U.S. Appl. No. 11/154,230, filed Jun. 16, 2005.
U.S. Appl. No. 11/154,863, filed Jun. 16, 2005.
U.S. Appl. No. 11/307,901, filed Feb. 27, 2006.
U.S. Appl. No. 11/307,900, filed Feb. 27, 2006.
U.S. Appl. No. 11/440,621, filed May 25, 2006.
U.S. Appl. No. 11/440,631, filed May 25, 2006.
U.S. Appl. No. 11/968,494, filed Jan. 2, 2008.
U.S. Appl. No. 11/968,496, filed Jan. 2, 2008.
U.S. Appl. No. 12/119,749, filed May 13, 2008.
U.S. Appl. No. 12/340,530, filed Dec. 19, 2008.
U.S. Appl. No. 12/495,497, filed Jun. 30, 2009.
U.S. Appl. No. 61/357,018, filed Jun. 21, 2010.
U.S. Appl. No. 12/849,960, filed Aug. 4, 2010.
U.S. Appl. No. 12/849,969, filed Aug. 4, 2010.
U.S. Appl. No. 12/849,977, filed Aug. 4, 2010.
U.S. Appl. No. 12/849,983, filed Aug. 4, 2010.
U.S. Appl. No. 12/849,991, filed Aug. 4, 2010.
U.S. Appl. No. 12/850,035, filed Aug. 4, 2010.
U.S. Appl. No. 12/850,063, filed Aug. 4, 2010.
U.S. Appl. No. 13/164,438, filed Jun. 20, 2011.
U.S. Appl. No. 13/335,220, filed Dec. 22, 2011.
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Boenisch, U.W. et al 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
CCPR Centro De Cirurgia Plastica e Reabilitacao 'Up Lifting (Aptos Threads) http://ccpr.com.br/up1-1.htm, Aug. 19, 2002 pp. 1-2.
Dahlin, Lars, "Techniques of Peripheral Nerve Repair", Scandinavian Journal of Surgery 97: 310-316, 2008.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Ingle, N.P. et al 'Mechanical Performance and Finite Element Analysis of Bidirectional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Khademhosseini, Ali et al., "Nanobiotechnology Drug Delivery and Tissue Engineering", Chemical Engineering Progress 102:38-42 (2006).
Lendelin, A. et al 'Biodegradable, Elastic Shape-Memory Polymers for Potential Biomedical Applications' (2002) Science vol. 296 pp. 1673-1676.
Lendelin, A. et al 'Shape-Memory Polymers' Agnew Chem Int. Ed. (2002) vol. 41 pp. 2034-2057.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Mullner, "Metal Foam Has a Good Memory", Dec. 18, 2007 Original story at <http://www.physorg.com/news117214996.html>.
Nie, Zhihong and Kumacheva, Eugenia, "Patterning surfaces with functional polymers", Nature Materials vol. 7(2008): 277-290.

(56) References Cited

OTHER PUBLICATIONS

Paul, Malcolm D. and Rui Avelar, "Quill™ SRS Techniques & Procedures A Novel Approach to Soft Tissue Approximation", Canada, Angiotech Pharmaceuticals, Inc., First Edition 82007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition 82008: 20 pages.
Paul, Malcolm D. nd Rui Avelar, "Quill™ SRS Techniques & Procedures a Novel Approach to Soft Tissue Approximation", Canada, Angiotech Pharmaceuticals, Inc., Third Edition 2009, 8 2007-2009: 27 pages.
Paul, Malcolm D., "Bidirectional Barbed Sutures for Wound Closure: Evoluation and Applications", Journal of the American College of Certified Wound Specialists (2009) 1, 51-57.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol=shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology (2001) No. 4 pp. 1-8.
Sulamanidze, M.A. et al 'Facial lifing with "Aptos" threads' http://fonendo.com (Jul. 18, 2001) pp. 1-4.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, MD, M.A., et al., "Soft tissue lifting in the mid-face: old philosophy, new approach-internal stitching technique (APTOS NEEDLE)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Tan E.L. et al., "A wireless, passive strain sensor based on the harmonic response of magnetically soft materials", Smart Materials and Structures 17 (2008): pp. 1-6.
Up Lifting (Aptos Threads), http://www.ccpr.com.br/up1-1.htm Aug. 19, 2002 pp. 1-2.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
2010 Physicians' Desk Reference.
Encyclopedia of Polymer Science and Engineering, edited by H.F. Mark, et al. Wiley-Interscience, New York, 1989.
Gross, Alex, "Physician perspective on thread lifts", Dermatology Times Feb. 27, 2002(2): 2 pages.
Gross, R.A. et al 'Biodegradable Polymers for the Environment' Science 297(5582) 803 (2002).
Immergut, Edmund H., Grulke, Eric A., Abe, Akihiro; Daniel R. 2005 John Wiley & Sons.
Jeong, H.E. et al 'A nontransferring dry adhesive with hierarchial polymer nanohairs' PNAS 106 (14) pp. 5639-5644 (2009).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Madhave et al 'A biodegradable and biocompatible gecko-inspired tissue adhesive' PNAS 105(7) pp. 2307-2312 (2008).
Manual for the Rubber Industry, 2nd ed. Bayer AG, Akron, Ohio, 1993.
Mark, J.E. ed. Physical Properties of Polymers Handbook. American Institute of Physics Press, Woodbury, N.Y., 1996.
Martin, D.P. et al 'Medical applications of poly-4-hydroxybutyrate: a strong flexible absorbable biomaterial' Biochemical Engineering Journal vol. 16 (2003) pp. 97-105.
Middleton and Tipton 'Synthetic Biodegradable Polymers as Medical Devices' (1998) Medical Plastics and Biomaterials Magazine.
Polymer Data Handbook, 1999 by Oxford University Press, Inc.
Polymer Handbook (4th Edition) edited by Brandrup, J. 1999.
The Vanderbilt Rubber Handbook, 3d ed. R.T. Vanderbilt Co., Norwalk, Conn., 1990.
European Search Report re: 10004453 dated Jun. 15, 2010.
European Search Report for EP10011872 dated Apr. 20, 2011.
European Search Report for EP10012437 dated Apr. 28, 2011.
International Preliminary Report re: PCT/US2008/087788 dated Jun. 22, 2010.
International Search Report for PCT/US1994/09631 dated Dec. 9, 1994.
International Search Report for PCT/US2002/20449 dated May 20, 2003.
International Search Report for PCT/US2003/030424 dated Nov. 1, 2004.
International Search Report for PCT/US2003/030664 dated May 25, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.

(56) References Cited

OTHER PUBLICATIONS

International Search Report for PCT/US2010/056898 dated Aug. 2, 2011.
International Search Report for PCT/US2010/060889 dated Oct. 11, 2011.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/059238 dated May 21, 2012.
International Search Report for PCT/US2011/060069 dated May 18, 2012.
International Search Report for PCT/US2012/030441 dated Sep. 27, 2012.
Supplementary European Search Report re: 03770556 dated Nov. 17, 2005.
Supplementary European Search Report re: 03754965 dated Nov. 18, 2005.
Supplementary European Search Report re: 05750101 dated Apr. 7, 2010.
Supplementary European Search Report re: 07017663 dated Nov. 7, 2007.

\* cited by examiner

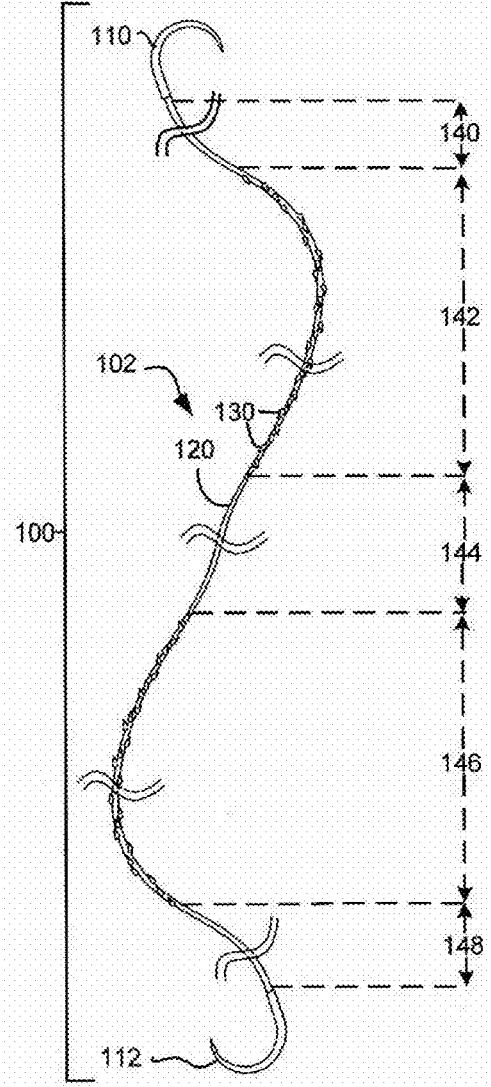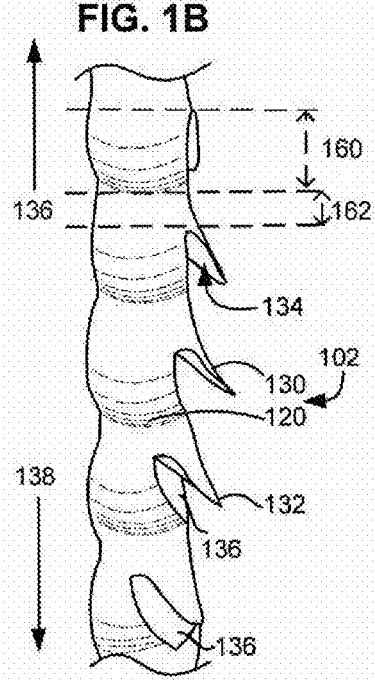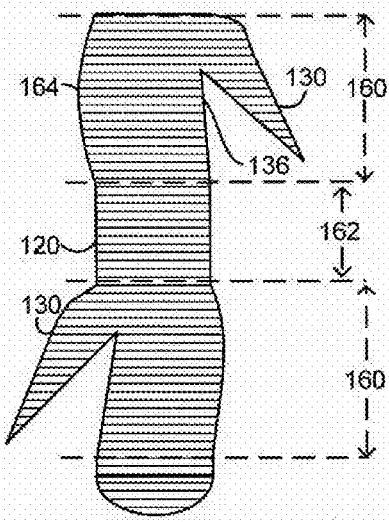

SELF-RETAINING SUTURE WITH VARIABLE DIMENSION FILAMENT AND METHOD

FIELD OF INVENTION

The present invention relates generally to self-retaining systems for surgical procedures, methods of manufacturing self-retaining systems for surgical procedures, and uses thereof.

BACKGROUND OF THE INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available, and the shape and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that constitutes the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can constitute a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. No. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and. 6,241,747). Although any number of sequential or intermittent configurations of retainers are possible, a common form of bidirectional self-retaining suture involves a needle at one end of a suture thread which has barbs having tips projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Projecting "away" from the needle means that the tip of the barb is further away from the needle and the portion of suture comprising the barb may be pulled more easily through tissue in the direction of the needle than in the opposite direction. Put another way, the barbs on both "halves" of a typical bidirectional self-retaining suture have tips that point towards the middle, with a transition segment (lacking barbs) interspersed between them, and with a needle attached to either end.

BRIEF SUMMARY OF THE INVENTION

Despite the multitude of advantages of unidirectional and bidirectional self-retaining sutures, there remains a need to improve upon the design of the suture such that a variety of common limitations can be eliminated. Specifically, several problems common to existing self-retaining sutures can be addressed by the embodiments of this invention, including, but not limited to: (i) retainers or barbs that are fragile and break or too flexible and bend back, or do not stand proud due to an insufficient ability of the material to plastically deform and as such do not properly engage when deployed in tissue; (ii) inadequate "hold" provided by the retainers for some surgical procedures; resulting in retainers or barbs do not sufficiently anchor in the surrounding tissue and "pull through;" (iii) insufficient contact between the retainers and the surrounding tissue (often occurring when the thread diameter is too small relative to the diameter of the hole created by a larger needle; this limits the ability of the retainers to contact and "grip" the surrounding tissue); (iv) breakage of the self-retaining suture during tensioning and wound approximation; and (v) rotation and slippage of the retainers after deployment. Furthermore, the creation and or deployment of retainer features of self-retaining sutures may be difficult to achieve.

Thus, it would be desirable to provide improved self-retaining sutures which have enhanced ability to anchor into the surrounding tissue, enhanced tissue holding capabilities, enhanced maximum load, and enhanced clinical performance.

It would further be desirable to provide improved methods for making self-retaining sutures that yield retainers which can be more readily created, elevated and deployed.

In accordance with the foregoing background and the limitations of the prior art, the present invention provides, improved self-retaining sutures which have enhanced ability to anchor into the surrounding tissue, enhanced tissue holding capabilities, enhanced maximum load, and enhanced clinical performance and methods for making such self-retaining sutures.

In accordance with another aspect, the present invention provides methods of making self-retaining sutures utilizing a variable-dimension filament which has variable cross-section.

In accordance with another aspect, the present invention provides self-retaining sutures including a variable-dimension filament having a larger amount of material in positions along the longitudinal axis and where retainers are formed at the positions having a larger amount of material.

In accordance with another aspect, the present invention provides sutures including a variable-dimension filament which has additional material at locations where retainers are formed such that the forming of retainers does not reduce the core cross-section of the filament.

In accordance with another aspect, the present invention provides sutures including a variable-dimension filament which forms a different distribution of material at some locations compared to other locations and where retainers are formed such that the retainers make use of the differently distributed material so as to minimize the impact of retainer formation upon the final tensile strength of the suture.

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

Features of the invention, its nature and various advantages will be apparent from the accompanying drawings and the following detailed description of various embodiments.

FIGS. 1A and 1B show a self-retaining suture system comprising a variable-dimension filament in accordance with an embodiment of the present invention.

FIG. 1C is a sectional view of the filament of the self-retaining suture system of FIGS. 1A and 1B illustrating the relationship between the variable-dimension filament and retainers.

DETAILED DESCRIPTION OF THE INVENTION

Definitions

Figure 2A:
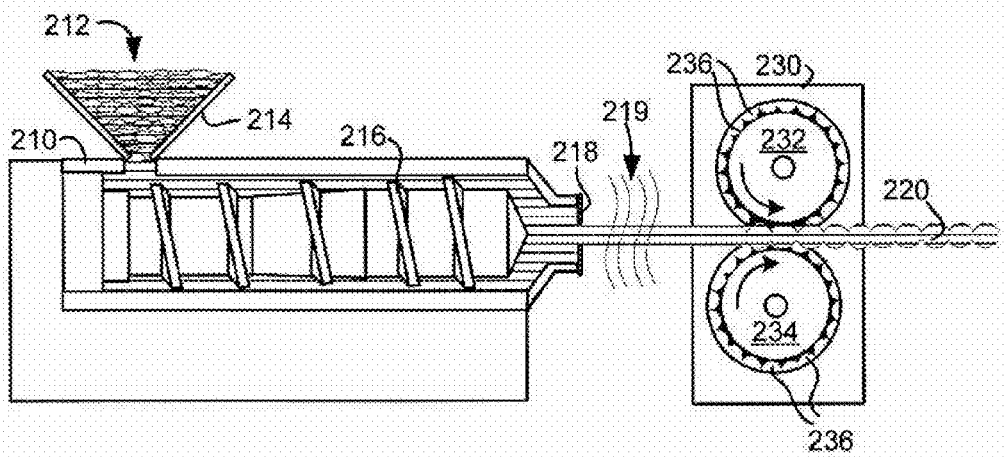
FIG. 2A illustrates a method and apparatus for making a variable-dimension filament suitable for creation of a self-retaining suture in accordance with an embodiment of the present invention.

Definitions of certain terms that may be used hereinafter include the following.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that includes features on the suture filament for engaging tissue without the need for a knot or suture anchor.

"Tissue retainer" (or simply "retainer") or "barb" refers to a physical feature of a suture filament which is adapted to mechanically engage tissue and resist movement of the suture in at least one axial directions. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the surgeon, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers may be configured to permit motion of the suture in one direction and resist movement of the suture in another direction without fanning out or deploying. In certain other configurations, the tissue retainer may be configured or combined with other tissue retainers to resist motion of the suture filament in both directions. Typically a suture having such retainers is deployed through a device such as a cannula which prevents contact between the retainers and the tissue until the suture is in the desired location.

"Retainer configurations" refers to configurations of tissue retainers and can include features such as size, shape, flexibility, surface characteristics, and so forth. These are sometimes also referred to as "barb configurations".

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two barb orientations.

"Transition segment" refers to a retainer-free (barb-free) portion of a bidirectional suture located between a first set of retainers (barbs) oriented in one direction and a second set of retainers (barbs) oriented in another direction. The transition segment can be at about the midpoint of the self-retaining suture, or closer to one end of the self-retaining suture to form an asymmetrical self-retaining suture system.

"Suture thread" refers to the filamentary body component of the suture. The suture thread may be a monofilament, or made of multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™[glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication Nos. 20020161168, 20040024169, and 20040116620. Sutures made from degradable suture material lose tensile strength as the material degrades. Degradable sutures can be in either a braided multifilament form or a monofilament form.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture deployment end" refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Armed suture" refers to a suture having a suture needle on at least one suture deployment end.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles are preferred.

Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and 5,464,422 (W. L. Gore, Newark, Del.); and 5,941,899; 5,425,746; 5,306,288 and 5,156,615 (US Surgical Corp., Norwalk, Conn.); and 5,312,422 (Linvatec Corp., Largo, Fla.); and 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

Self-Retaining Suture Having Variable-Dimension Filament

As discussed above, the present invention provides compositions, configurations, methods of manufacturing and methods of using self-retaining systems in surgical procedures which increase the ability of the self-retaining sutures to anchor into the surrounding tissue to provide superior holding strength and improve clinical performance. In accordance with one embodiment, the present invention contains a self-retaining suture which is composed of a variable-dimension filament.

A. Self-Retaining Suture System

FIG. 1A illustrates a bidirectional self-retaining suture system 100. Self-retaining suture system 100 includes needles 110, 112 attached to self-retaining suture thread 102. Self-retaining suture thread 102 includes a plurality of retainers 130 distributed on the surface of a variable-dimension filament 120. In lead-in region 140 of variable-dimension filament 120 there are no retainers 130. In region 142 of variable-dimension filament 120 there are a plurality of retainers 130 arranged such that the suture can be deployed in the direction of needle 110, but resists movement in the direction of needle 112. In transition region 144, there are no retainers 130. In region 146 of variable-dimension filament 120 there are a plurality of retainers 130 arranged such that the suture can be deployed in the direction of needle 112, but resists movement in the direction of needle 110. In lead-in region 148 of variable-dimension filament 120 there are no retainers 130. A break is shown in each of regions 140, 142, 144, 146 and 148 to indicate that the length of each region may be varied and selected depending upon the application for which the suture is intended to be used. Although a bidirectional self-retaining suture system 100 is illustrated, the present invention includes self-retaining suture systems of a wide variety of retainer and needle configurations as described above. Likewise, although needles 110 and 112 are shown as curved needles, needles 110 and 112 can be any of the range of different surgical needles developed for use in different applications. Needles 110 and 112 may have the same configuration or different configurations.

FIG. 1B illustrates a magnified view of self-retaining suture thread 102 in region 142. As shown in FIG. 1B, a plurality of retainers 130 is distributed on the surface of variable-dimension filament 120. Variable-dimension filament 120 has a variable-dimension cross-section and has additional material in retainer regions 160 as compared to inter-retainer regions 162. The retainers 130 are made by making a cut 136 into the variable-dimension filament 120 in the regions 162 where there is increased volume of material. Each retainer 130 is cut into a region 160 of the variable-dimension filament 120 so that the minimum cross-section of the variable-dimension filament remaining in the region of the retainer 130 is: (1) larger than the minimum cross-section would be if a uniform filament were used, and/or (2) larger than or equal to the cross-section of the inter-retainer regions. Accordingly, the tensile strength of the suture is maintained and/or any reduction in tensile strength caused by formation of the retainers is minimized.

The affixation of self-retaining sutures after deployment in tissue entails the penetration of retainer ends into the surrounding tissue resulting in tissue being caught between the retainer and the suture body. The inner surface of the retainer that is in contact with the tissue that is caught between the retainer and the suture body, herein referred to as the "tissue engagement surface" or "inner retainer surface," can be adapted to better engage the tissue. As illustrated in FIG. 1B, each retainer 130 has a tip 132 and a tissue retainer surface 134. When self-retaining suture thread 102 is moved in the direction of arrow 136, each retainer 130 lies flat against the body of variable-dimension filament 120. However, when self-retaining suture 102 is moved in the direction of arrow 138, tip 132 of each retainer 130 engages tissue surrounding variable-dimension filament 120 and causes each retainer 130 to fan out from variable-dimension filament 120 and engage the tissue with face 134 thereby preventing movement of the suture in that direction. The engagement of the retainers 130 with the tissue is also enhanced where, as here, the retainer is located in a region of variable-dimension filament 120 where there is an increased cross-section.

FIG. 1C shows a schematic cross-sectional view of variable-dimension filament 120 having retainers 130. Variable-dimension filament 120 has a variable-dimension cross-section and has additional material 164 in retainer regions 160 as compared to inter-retainer regions 162. As can be seen from FIG. 1C, the diameter (thickness) of filament 120 in the region of cut 136 is made larger by the presence of the additional material 164 in region 160 as compared to region 162. Thus the minimum cross-sectional area of the suture thread 102 is larger for variable-dimension filament 120 than it would be for a filament comprising the same total amount of material uniformly distributed—all other things being equal.

B. Manufacture of Variable-Dimension Filament

Figure 2B:
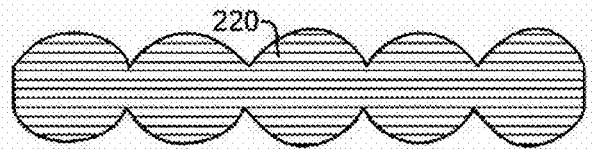
FIGS. 2B and 2C illustrate different configurations of variable-dimension filament which may be made with the apparatus and method of FIG. 2A.
Figure 2C:
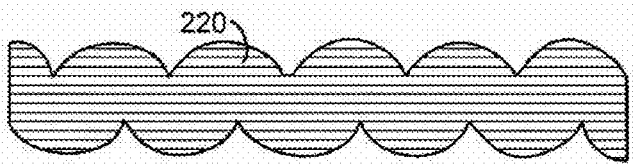

In accordance with one embodiment of the invention, a monofilament 220 is formed by extrusion and coining. As shown in FIG. 2A, an extruder 210 receives pellets of polymer 212 in hopper 214. The polymer is melted and pushed by screw 216 through extrusion die 218 to form filament 220 of melted polymer 212. The filament 220 initially has a uniform cross-section in the shape of the hole in the extrusion die 218. Typically monofilament is extruded with a uniform circular cross-section, but it may be extruded in any shape such as triangular square or any other polygon regular or otherwise. The extruded filament passes through an air gap 219 where the filament cools and polymer 212 solidifies somewhat. The extruded filament 220 is passed to coining machine 230 where filament 220 passes between two rollers 232, 234. The filament may be twisted or rotated after passing between rollers 232, 234 such that the coining pattern rotates around the finished filament. The filament may optionally be quenched, drawn and/or tempered before and/or after the coining process. Rollers 232, 234 have a patterned surface which presses the material of filament 220 into the desired variable-dimension configuration. This coining process can be conducted at a temperature that is between 20-80% of the melting point of the polymer (Celsius). In preferred embodiments, the coining process is conducted at temperatures above the glass transition temperature of the polymer and below the onset of melting temperature. In the configuration illustrated in FIG. 2A, each of rollers 232, 234 has a repeating pattern of hemispherical indentations 236 on its outer surface such that as filament 220 passes through the rollers is takes on the shape shown in FIG. 2A. Depending upon the phase alignment of rollers 232, 234 a number of different patterns of variable-dimension filament 220 may be achieved. If the indentations of the rollers 232, 234 are in phase, filament 220 shown in FIG. 2B is the result. If the indentations of rollers 232, 234 are out of phase then the filament 220 of FIG. 2C is the result.

However, the coining pattern on rollers 232, 234 may be any shape desired to be imprinted upon filament 220. The final configuration of filament 220 will depend upon the coining pattern and the phase of the rollers. Additional coining steps may be carried out sequentially with the final pattern imposed by a series of coining rollers at different temperatures to better memorize the final configuration of the filament. Additionally, the input to coining machine may be different than shown. For example filament 220 may be a co-extrusion of two or more polymer. In either case, the filament may be shaped in whole of in part by the hot coining process. Particular apparatus and methods for forming co-extruded monofilaments suitable for use in the present invention can be found in U.S. Pat. No. 7,070,610 titled "Monofilament Suture And Manufacturing Method Thereof" to Im et al. and U.S. Pat. No. 6,315,788 titled "Materials And Surgical Articles Made Therefrom" to Roby both of which are incorporated herein by reference.

Figure 2D:
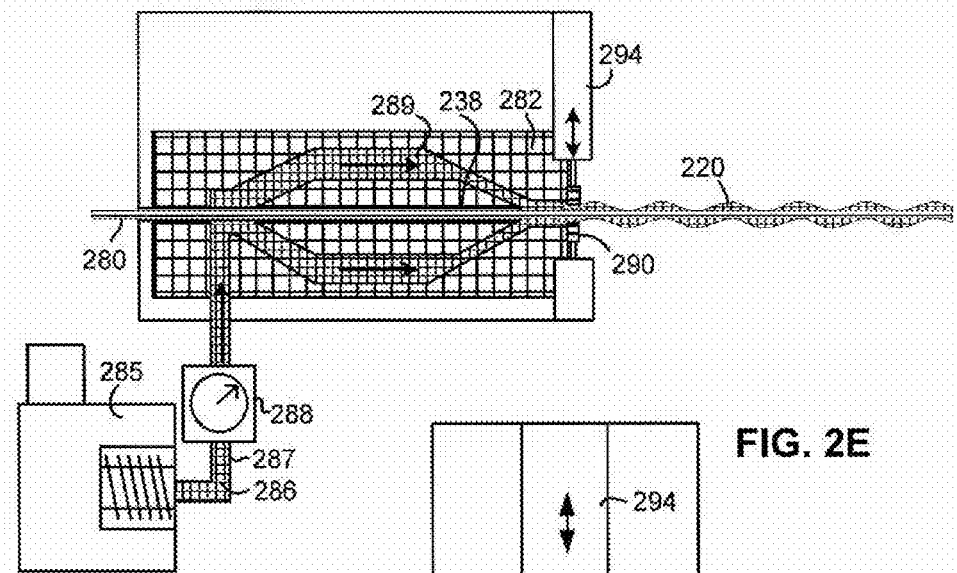
FIGS. 2D and 2E provide two views of an alternative method and apparatus for making a variable-dimension suitable for creation of a self-retaining suture in accordance with an embodiment of the present invention.
Figure 2E:
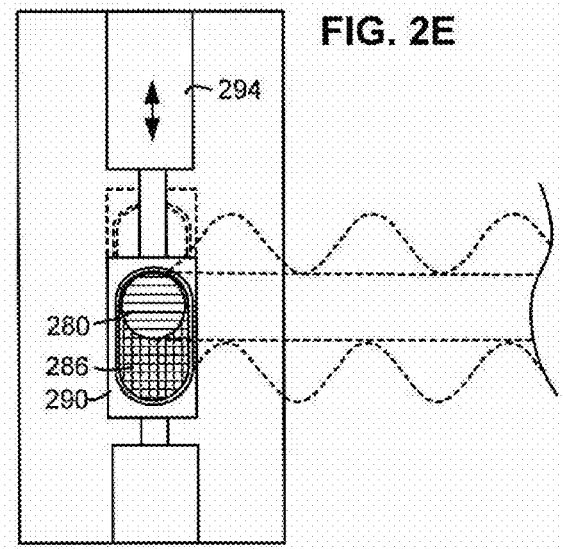
Figure 2F:
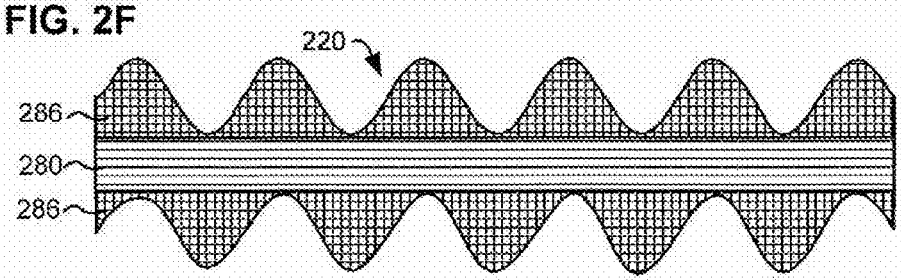
FIG. 2F illustrates the configuration of a variable-dimension filament which may be made with the apparatus and method of FIGS. 2D and 2E.

FIG. 2D illustrates an alternative method of making a filament suitable for use in embodiments of the present invention. As shown in FIG. 2D, a core filament 280 is drawn through an extrusion die 282. Satellite extruder 285 heats, melts and extrudes a sheath material 286 via conduit 287 to die 282. Metering pump 288 controls the flow of sheath material 286 to flow path 289 of die 282. The rate of supply of sheath material 286 and the rate of movement of core filament 280 are controlled such that a sheath material 286 is coated on the core filament 280 in the desired cross-section (as determined by the cross-section of the extrusion plate 290. Suitable methods for making a filament comprising a core coated with an extruded material is described in U.S. Pat. No. 6,183,499 titled "Surgical Filament Construction" to Fisher et al. which is incorporated herein by reference. Extrusion plate 290 is oscillated by actuator 294 such that the thickness of the coating varies from side to side of core filament 280—in this case according to a sinusoidal pattern. FIG. 2E shows an end-on view of extrusion plate 290. As extrusion plate 290 is oscillated by actuator 294, polymer coating is shifted to either side of core filament 280 resulting in the extrusion pattern illustrated by the dashed lines. Note that in this embodiment, the cross-sectional area does not vary because the shape of the aperture in extrusion plate 290 does not change. However, the distribution of material 286 about filament 280 does vary along the length of filament 280. FIG. 2F shows a cross-section of a filament 220 that can be made using the apparatus and method of FIGS. 2D, 2E. FIG. 2F shows the sinusoidal variation in the distribution of material 286 relative to core filament 280.

The finished filament 292 consisting of core filament 280 and sheath material 286 may be quenched, tempered and drawn and then wound onto a drum as shown in FIG. 2A. However, in certain embodiments, core filament 280 may already have been drawn and no further drawing of finished filament 292 may be necessary or desirable. In some embodiments, for example, a core filament of a core material may be extruded and then drawn. Then the same material may be extruded over the core filament (as shown in FIG. 2B) without subsequent drawing of the filament. Moreover, extrusion coating of a preformed filament may also be utilized in conjunction with the coining process illustrated in FIG. 2A whereby the distribution of the coating layer on the filament is caused to take on the desired distribution by operation of the coining rollers instead of or in addition to the variation in the extrusion process.

In an alternative embodiment rather than oscillating die plate 290, the filament 280 may instead be oscillated during the extrusion process. This alternative—because of the lower, inertia of the filament compared to the die plate 290 may allow for greater control over the extrusion process and allow for a variation in the coating thickness at a greater number of cycles per unit length of filament. The location of the sheath material may also be varied by twisting or rotating core filament 280 during the extrusion of sheath material 286 (instead of or in addition to oscillating extrusion plate 290) such that the location of the additional material rotates around the finished filament in a spiral pattern. Similarly extrusion plate 290 may be rotated around core filament 280 in addition to oscillating from side to side. Alternatively core filament 280 may be rotated and/or twisted during extrusion of sheath material 286 such that the sheath material 286 takes on a twisted/spiral configuration when the core filament 280 is relaxed.

Figure 2G:
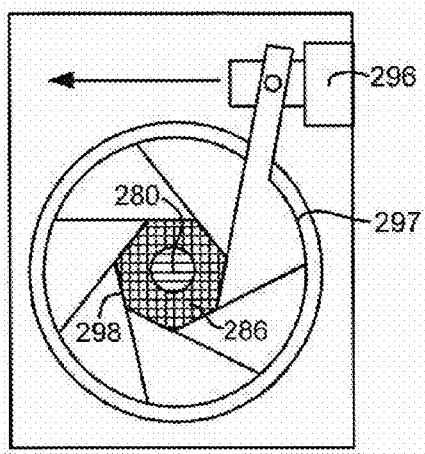
FIGS. 2G and 2H provide two views of a variable aperture extrusion plate for making a variable-dimension suitable for creation of a self-retaining suture in accordance with an embodiment of the present invention.
Figure 2H:
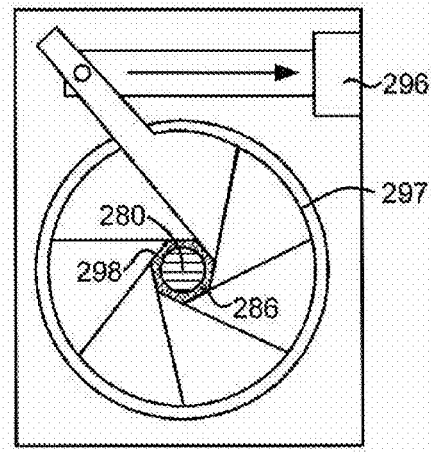
Figure 2I:
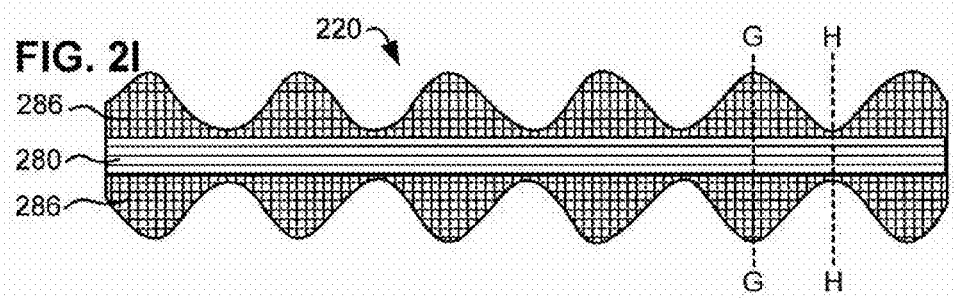
FIG. 2I illustrates the configuration of a variable-dimension filament which may be made with the apparatus and method of FIGS. 2G and 2H.

In alternative embodiments a variable-dimension filament may be made utilizing an extrusion plate which has a variable aperture size by varying the aperture size as the filament and or filament coating is extruded. For example, the extrusion plate 290 may have a structure like the iris diaphragm of a camera. As shown in FIG. 2G and FIG. 2H an iris diaphragm 297 is operated by actuator 296. Actuator 296 operates iris diaphragm 297 to open and close aperture 298. FIG. 2G shows aperture 298 in an open position whereas FIG. 2H shows aperture 298 in a closed position. Actuator 296 operates to open and close aperture 298 as a filament 220 is extruded. FIG. 2I shows a cross-section through a filament that may be made using the apparatus of FIGS. 2G, 2H. Note that the amount of sheath material 286 extruded over core filament 280 varies along the length of the finished filament 280. Dashed line G-G shows the cross-section extruded when iris diaphragm 297 is in the position shown in FIG. 2G. Dashed line H-H shows the cross-section extruded when iris diaphragm 297 is in the position shown in FIG. 2H.

Figure 2J:
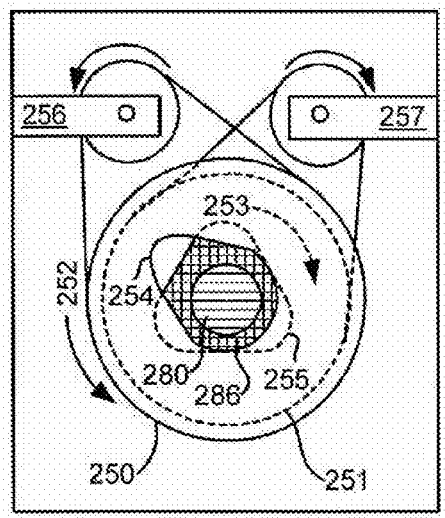
FIG. 2J illustrates an alternative variable aperture extrusion plate for making a variable-dimension filament suitable for creation of a self-retaining suture in accordance with an embodiment of the present invention.

Many methods of creating a variable aperture may be utilized to create a variable-dimension filament. In an alternative embodiment, as shown in FIG. 2J two extrusion plates 250, 251 are rotated in opposite directions 252, 253. Each extrusion plate has an aperture 254, 255. The apertures 254, 255 are different shapes. The shape of apertures 254, 255 are selected such that more of material 286 is extruded over filament 280 at certain phases of relative rotation of extrusion plates 250, 251 than at other phases of relative rotation of extrusion plates 250, 251. Each extrusion plate 250, 251 is driven by a different actuator 256, 257. The frequency and location of sites having greater extruded material along a filament 220 may be controlled by controlling the rates of rotation of extrusion plates 250, 251 and the shapes of the apertures 254, 255. Such variable apertures may be utilized to extrude a variable dimension filament 220 with or without a preformed core filament 280.

The manufacturing technique illustrated in FIGS. 2D-2J in which a sheath is extruded over a core filament has the advantage that the core filament 280 can be treated to strengthen the filament by drawing and tempering prior to extrusion of the variable coating layer. Furthermore, the coating polymer may be selected for its ability to enhance the formation, elevation and/or deployment of the retainers on the finished suture filament. Thus, the polymer may be selected for different properties than core filament 280 which can be selected primarily to impart high tensile strength to the finished filament. In some filaments the core and sheath are the same material, however, the sheath material has different physical properties than the core material because the sheath material has not undergone the drawing process whereas the core has been drawn—during the drawing process, a polymer typically loses a large portion of its plasticity as a trade off for higher elastic modulus. For example, in some embodiments it is preferable to use a coating layer which, either because it is a different polymer than the core or because it is the same polymer but differently treated, is more easily plastically deformed than would be the material of the core. This facilitates elevation of the retainers by the method shown for example in FIG. 2C because the retainers do not recoil substantially after elevation.

Although extrusion processes have been illustrated in FIGS. 2A through 2J, any suitable manufacturing process may be used to form the variable-dimension filament utilized as a stock filament material for embodiments of the present invention. For example, variable dimension filaments as described herein may be produced by methods, including without limitation, injection molding, stamping, cutting, laser, dip coating, chemical deposition coating and so forth. The dimensions of the extruded filament may also be varied by cyclically adjusting the rate of extrusion and/or the speed of the rollers which take-up and/or draw the filament (godets).

C. Retainer Formation and Elevation on a Variable-Dimension Filament

Figure 3A:
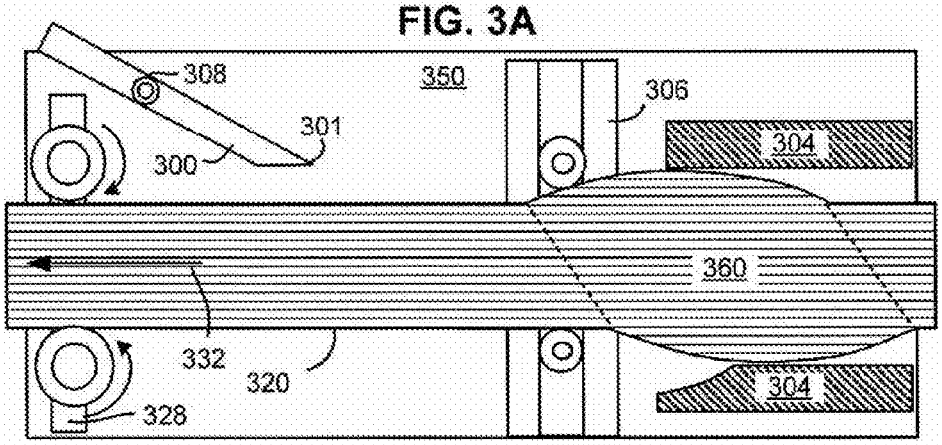
FIGS. 3A, 3B and 3C provide sequential views illustrating an apparatus and method for cutting a retainer in a variable-dimension filament to create a self-retaining suture thread in accordance with an embodiment of the present invention.
Figure 3B:
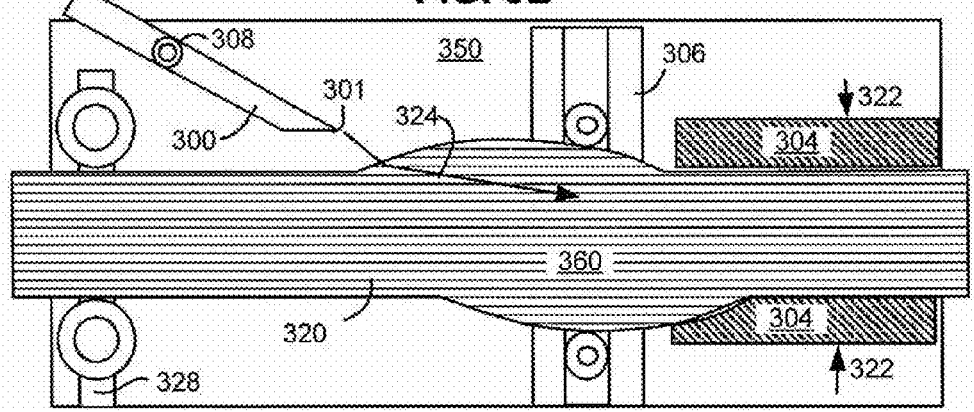
Figure 3C:
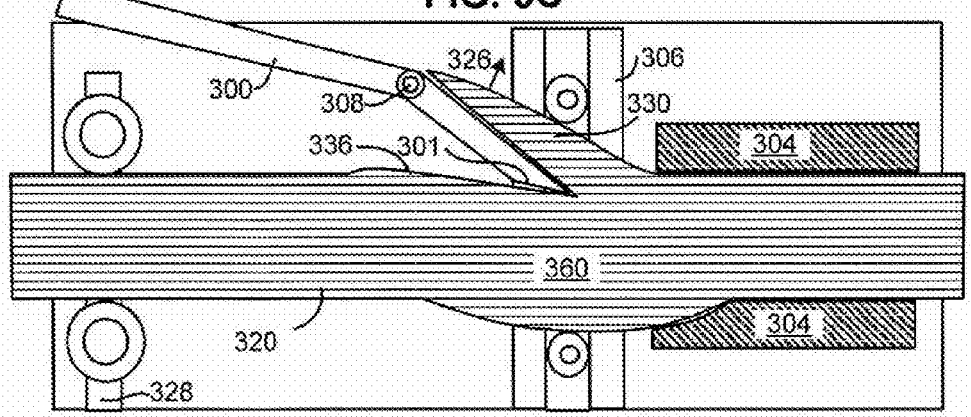

In certain embodiments, retainers may be formed on a variable-dimension filament in a process subsequent to manufacturing the variable-dimension filament. One way to form retainers on a variable-dimension filament is by cutting into the variable-dimension filament as illustrated in FIGS. 3A-3C. Retainers may be hand-cut, laser-cut, or machine-cut using blades, cutting wheels, grinding wheels, and so forth. During cutting either the cutting device or the suture may be moved relative to the other, or both may be moved, to control the location, size, shape, angle, and depth of cut 310. Particular methods for cutting barbs on filaments are described in U.S. Pat. No. 7,225,512 titled "Method Of Forming Barbs On A Suture And Apparatus For Performing Same" to Genova et al., and U.S. patent application Ser. No. 10/065,280 titled "Barbed Sutures" to Leung et al. both of which are incorporated herein by reference. However, where retainers are cut on a variable-dimension filaments in particular, steps must be taken to register the filament prior to cutting the retainers in order that the cutting process make use of the attributes of the variable-dimension filament to achieve enhanced minimum cross-section and thus enhanced tensile strength.

Referring now to FIGS. 3A, 3B and 3C where an exemplary process for cutting a retainer 330 on a variable-dimension filament 320 with a cutting machine 350 is provided. FIG. 3A shows a longitudinal cross-section of variable-dimension filament 320. As shown in FIG. 3A variable-dimension filament 320 consists of additional material in region 360 of variable-dimension filament 320. In order to make a cut 336 in the region 360 it is first necessary to advance variable-dimension filament 320 into the correct position in which region 360 is appropriately positioned relative to cutting mechanism 300. As shown schematically in FIG. 3A, variable-dimension filament 320 is advanced (indexed) in the direction of arrow 332 relative to a cutting bed vise 304, a sensor 306 and blade 300 by an indexing mechanism 328. Variable-dimension filament 320 may be advanced by an indexing mechanism 328 that includes devices such as rollers or drums or other actuators suitable for moving filament with the accuracy necessary to position region 360 relative to a cutting bed and blade. The variable-dimension filament may also be rotated/twisted by a suitable mechanism during the cutting process so as to distribute the retainers around the circumference of the suture. Sensor 306 monitors the diameter of variable-dimension filament 320 as variable-dimension filament 320 moves in the direction of arrow 320. Sensor 306 may be a mechanical sensor such as rollers in contact with variable-dimension filament 320 or may be a contactless optical or other electrical sensor system that is capable of measuring the dimensions of variable-dimension filament 320 as it passes through cutting machine 350. When sensor 306 detects that region 360 is correctly registered relative to blade 301 for making a cut 336, the movement of variable-dimension filament 320 is stopped.

As shown in FIG. 3B, when sensor 306 detects that region 360 is correctly registered relative to blade 301 for making a cut 336, the movement of variable-dimension filament 320 is stopped and cutting bed vise 304 is positioned so as to support variable-dimension filament 320. Cutting bed vise 304 moves in the direction of arrows 322 to clamp variable-dimension filament 320. In this embodiment cutting bed vise 304 may be servo-operated, in other embodiments cutting bed vise 304 may be operated by a spring, cam, solenoid, pneumatic actuator or the like. The operation of cutting bed vise 304 is synchronized with the indexing mechanism 328 for advancing the suture thread and the cutting mechanism 300 for cutting the retainers.

With variable-dimension filament registered and supported by cutting bed vise 304, a cutting mechanism 300 is operated to move blade 301 along a cut path 324 into the variable-dimension filament 320. The blade 301 is operated by an actuator. Suitable actuators may include a motor, cam, solenoid, pneumatic actuator or the like. In certain embodiments, cut path 324 may be modified based on the dimensions of the particular region 360 registered for cutting. For example, it may be desirable that cut path 324 leaves a certain minimum cross-section in filament 320. Thus, cut path 324 may be adjusted so as to adjust the depth of cut 336 based upon the cross-section of material actually present at a particular point along the suture. This provides additional control by adjusting the cut parameters based upon the measured dimensions of the variable-dimension filament 320 to deal with manufacturing variations from one region 360 to another region 360 in variable-dimension filament 320. FIG. 3C shows the cut 336 made in the variable-dimension filament 320 by advancement of blade 301 along cut path 324.

After cut 336 has been made, blade 301 rotates about pivot 308 to push newly created retainer 330 further in the direction of arrow 326. This action elevates retainer 330 by plastically-deforming the material at the base of retainer 330, such that retainer 330 remains elevated above the surface of variable-dimension filament 320 after removal of blade 301. This elevation may be achieved using blade 301 or a separate elevating component or machine. The elevation may also be achieved in a separate process or in some case automatically because of properties of the material of variable-dimension filament 320. After elevating retainer 330, blade 301 is withdrawn, cutting bed vise 304 is caused to release variable-dimension filament 320, and variable-dimension filament 320 is advanced again until another region 360 is registered for cutting a new retainer as shown in FIG. 3A.

D. Filament Configurations

Depending upon the configuration of the extruders, die, spin block, spinneret, or other manufacturing equipment, a filament suitable for creating a self-retaining suture in accordance with embodiments of the present invention can be created with a wide variety of different arrangements of different materials. Furthermore, filaments can be made using 2, 3, 4 or even more different component materials if necessary or desired for the particular application. Different configurations of filaments are useful in specific embodiments of the present invention and are described below with respect to FIGS. 4A-4E.

Figure 4A:
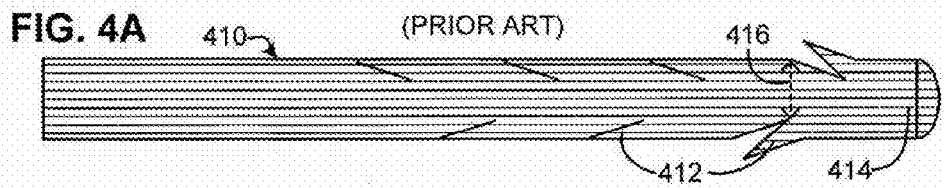
FIG. 4A illustrates a prior art uniform filament.

FIG. 4A illustrates a prior art self-retaining suture in 410 which retainers 412 are cut in a filament 414 of uniform cross-section. It should be noted that the minimum cross-section 416 of the filament that remains after the retainers has been cut is significantly reduced compared to the cross-section of the uncut filament.

Figure 4B:
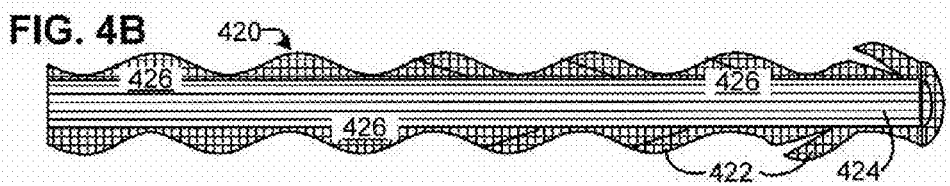
FIGS. 4B-E illustrate alternative configurations of variable-dimension filaments suitable for creation of a self-retaining suture in accordance with different embodiments of the present invention.

FIG. 4B illustrates a portion of a self-retaining suture 420 according to an embodiment of the present invention. In self-retaining suture 420 of FIG. 4B, retainers 422 are cut in a filament 424 which has a sinusoidal variation in the distribution of material. In the filament 420 of FIG. 4B the cross-sectional area does not vary along the length of the filament but the distribution of material changes in position. Retainers 422 are cut into the filament so as to utilize the regions where the material is distributed 426. After the retainers 422 are cut, the minimum cross-section of the filament remaining is significantly larger than for the uniform filament of FIG. 4A. The minimum cross-section will be larger even where the volume of material in the filament is equivalent. Thus, the configuration of FIG. 4B results in a larger minimum cross-section after retainer cutting for the same volume material. This results in a higher tensile strength for a given suture size than would be possible with a uniform filament. Although a sinusoidal distribution has been illustrated other period, aperiodic variable distributions may be utilized.

Figure 4C:
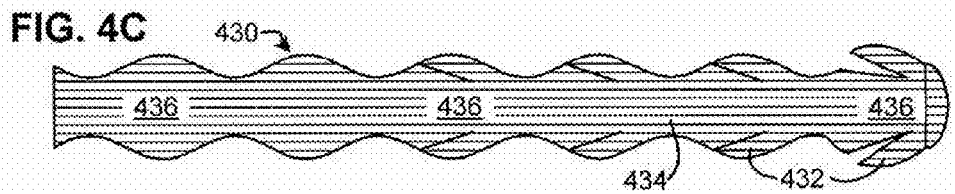

FIG. 4C illustrates a second embodiment of a self-retaining suture 430 according to an embodiment of the present invention. In self-retaining suture 430 of FIG. 4C, retainers 432 are cut in a filament 434 which has a sinusoidal variation in the distribution of material. In the suture 430 of FIG. 4C the cross-sectional area varies along the length of the filament. Retainers 432 are cut into the filament 434 so as to utilize the regions of additional material 436. After the retainers 432 are cut, the minimum cross-section of the filament remaining is significantly larger than for the uniform filament of FIG. 4A. The minimum cross-section will be larger even where the volume of material in the filament is equivalent. Thus, the configuration of FIG. 4C results in a larger minimum cross-section after retainer cutting for the same volume material. This results in a higher tensile strength for a given suture size than would be possible with a uniform filament. Although a sinusoidal distribution has been illustrated other period, aperiodic variable distributions may be utilized.

Figure 4D:
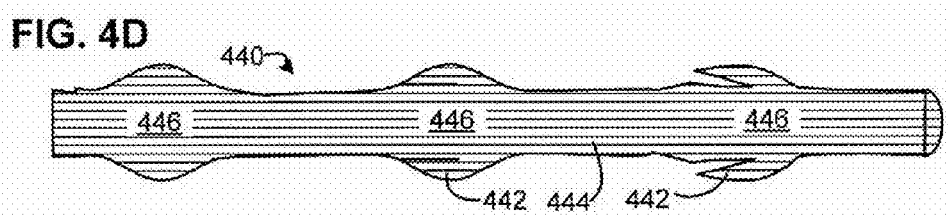

FIG. 4D illustrates a third embodiment of a self-retaining suture 440 according to an embodiment of the present invention. In self-retaining suture 440 of FIG. 4D, retainers 442 are cut in a filament 444 which has a non-sinusoidal variation in the distribution of material. Retainers 442 are cut into the filament so as to utilize the regions of additional material 446. After the retainers 442 are cut, the minimum cross-section of the filament remaining is significantly larger than for the uniform filament of FIG. 4A. The minimum cross-section will be larger even where the volume of material in the filament is equivalent. Thus, the configuration of FIG. 4D results in a larger minimum cross-section after retainer cutting for the same volume material. This results in a higher tensile strength for a given suture size than would be possible with a uniform filament.

Figure 4E:
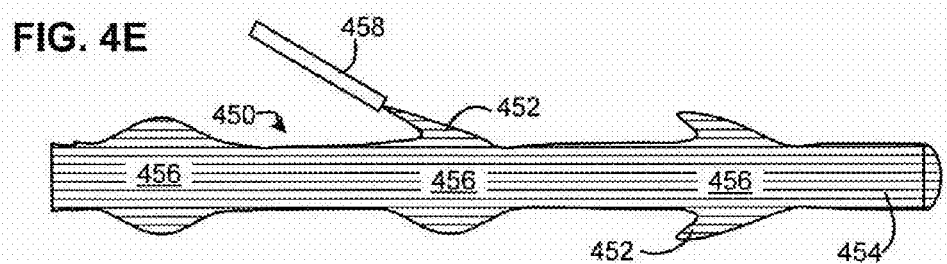

FIG. 4E illustrates a fourth embodiment of a self-retaining suture 450 according to an embodiment of the present invention. In self-retaining suture 450 of FIG. 4E, retainers 452 are formed by localized melting of filament 454 which has a sinusoidal variation in the distribution of material. Retainers 452 are formed by melting the filament and the melted filament material is drawn out by tool 458. Forming the retainers 452 in this manner requires material and consequently the amount of material remaining in the filament is reduced surrounding the retainers 452. However, the retainers 452 are formed in the regions 456 where extra material having extra material. Thus, even after the retainers 452 are formed, the minimum cross-section of the filament remaining is as large as or larger than the cross-section of the filament in the inter-retainer regions. Thus the configuration of FIG. 4E results in a larger minimum cross-section after retainers 452 are formed for the same volume of material. This results in a higher tensile strength for a given suture size than would be possible with a uniform filament.

E. Filament Materials

The configuration of the materials in the filament will depend upon the characteristics of the material or materials and the amount of material necessary to fulfill the role of the filament. For example, in some embodiment the outer layer may be a different material than the inner layer with the outer layer chosen to have enhanced plasticity in order that barbs may more easily formed and elevated from the surface of the filament. The depth of the outer layer may be varied using the manufacturing methods discussed above such that the retainers when formed are formed entirely out of the outer material. Likewise in one embodiment of the present invention the material of a core is chosen because of its characteristic of tensile strength. The strength of the final filament material will depend in large part upon the cross-sectional area of the core filament. Thus core filament should be as large as possible while providing sufficient amount of sheath material 410 to permit the formation of retainers. The diameter of the material is also constrained as the suture based upon the surgical needs.

Suitable materials for sutures and/or core filaments of sutures include materials that are currently used for making sutures. These materials are characterized by high yield strength after drawing and sufficient flexibility to ease handling. One suitable material is copolymer of glycolide and c-caprolactone, in a ratio of 50/50 to 95/5. More preferably the ratio of glycolide to c-caprolactone is between preferably 70/30 to 80/20 and most preferably between 72/28 and 78/22. Suitable non-degradable suture materials for the core material include polyamide (also known as nylon, such as nylon 6 and nylon 6.6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Suitable absorbable materials for the core include polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group)

Because the retainers are formed from the outer material or sheath layer, those layers may incorporate materials that promote the formation and elevation of the retainers while the core is made of a material or materials which enhances the yield strength of the filament. Materials that are suitable for retainer formation are characterized by having a sufficiently small elastic zone and sufficiently large plastic zone to allow for permanent deformation of barbs from the prone position during cutting and elevation and low recoil after elevating the barbs. Ideally, the retainers formed from the sheath material are stiff, i.e. the retainer material has a high elastic constant, but short elastic zone, and a long plastic zone. So the retainers take a lot of strength to plastically deform, but once the retainer is deformed the retainer retains the shape. Additionally the sheath material should have sufficient flexural strength to prevent barbs from bending backwards during fixation of the suture in the tissues and sufficient strength to prevent barbs from breaking during fixation of the suture in the tissues. For example, suitable materials for a sheath include Nylon 6,6, polydioxanone, polypropylene, non drawn polycaprolactone, poly-4-hydroxybutyl lactone, non drawn polydioxanone. Thus, in some embodiments a sheath of non-drawn polymer may be extruded over a core of the same polymer which has already been drawn thus yielding a suture of a single polymer having a more plastic sheath over a high strength core owing to the disparate treatment of the two components.

Additionally, self-retaining sutures described herein may be provided with therapeutic compositions including, for example, compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) constructing the suture itself with a composition. Such compositions may include without limitation anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). The purpose of the suture may also determine the sort of coating that is applied to the suture; for example, self-retaining sutures having anti-proliferative coatings may be used in closing tumor excision sites, while self-retaining sutures with fibrosing coatings may be used in tissue repositioning procedures and those having anti-scarring coatings may be used for wound closure on the skin. As well, the structure of the suture may influence the choice and extent of coating; for example, sutures having an expanded segment may include a fibrosis-inducing composition on the expanded segment to further secure the segment in position in the tissue. Coatings may also include a plurality of compositions either together or on different portions of the suture, where the multiple compositions can be selected either for different purposes (such as combinations of analgesics, anti-infective and anti-scarring agents) or for the synergistic effects of the combination.

F. Clinical Uses

In addition to the general wound closure and soft tissue repair applications, self-retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. The microsutures may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self-retaining sutures can be used in a variety of veterinary applications for a wide number of surgical and traumatic purposes in animal health.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A surgical suture comprising an elongated filament, the elongated filament comprising:
    a plurality of first locations along a length of the elongated filament where a retainer is cut in the filament at each of the first locations, a first filament cross-sectional area present at each of the first locations, where the first filament cross-sectional areas are identical at each of the first locations;
    a plurality of second locations interspersed with the plurality of first locations, where a retainer has not been cut in the filament at any of the second locations, a second filament cross-sectional area present at each of the second locations, where the second filament cross sectional areas are identical at each of the second locations;
    the first filament cross sectional area being larger than the second filament cross sectional area; and
    each retainer having a tissue-penetrating end.

2. The surgical suture of claim 1 which is a degradable suture.

3. The surgical suture of claim 1 which is a non-degradable suture.

4. The surgical suture of claim 1 which is a bidirectional suture.

5. The surgical suture of claim 1 which is a unidirectional suture.

6. The surgical suture of claim 1 in combination with at least one needle.

7. The surgical suture of claim 6 wherein a plurality of retainers are arranged such that the suture can be deployed in the direction of the needle located at a deployment end of the suture but resists movement of the suture in an opposite direction.

8. The surgical suture of claim 1 wherein the retainers lie flat when pulled through tissue in a deployment direction of the suture and fan out when the suture is pulled through tissue in a direction contrary to the deployment direction.

9. The surgical suture of claim 1 having a circular periphery at each of the first and second locations.

10. The surgical suture of claim 1 further comprising a therapeutic composition.

11. The surgical suture of claim 1 further comprising a lubricious agent.

12. The surgical suture of claim 1 fully coated with a therapeutic composition.

13. The surgical suture of claim 1 selectively coated with a therapeutic composition.

* * * * *